United States Patent

Hammon et al.

Patent Number: 5,264,625
Date of Patent: Nov. 23, 1993

[54] CATALYTIC GAS-PHASE OXIDATION OF ACROLEIN TO ACRYLIC ACID

[75] Inventors: Ulrich Hammon, Karlsruhe; Klaus Herzog, Ludwigshafen; Hans-Peter Neumann, Mannheim, all of Fed. Rep. of Germany

[73] Assignee: BASF Aktiengesellschaft, Ludwigshafen, Fed. Rep. of Germany

[21] Appl. No.: 946,173

[22] Filed: Sep. 17, 1992

[30] Foreign Application Priority Data

Sep. 27, 1991 [DE] Fed. Rep. of Germany ....... 4132263

[51] Int. Cl.$^5$ .................. C07C 51/25; C07C 57/04; C07C 57/055
[52] U.S. Cl. .................. 562/532; 562/534; 562/535; 562/536; 562/544; 562/546; 562/548; 562/600
[58] Field of Search ............ 562/532, 534, 535, 536, 562/544, 546, 548, 600

[56] References Cited

U.S. PATENT DOCUMENTS

| | | | |
|---|---|---|---|
| 3,801,634 | 4/1974 | Krabetz et al. | 260/533 N |
| 3,865,873 | 2/1975 | Oda et al. | 260/530 N |
| 4,075,127 | 2/1978 | Kadowaki et al. | 252/470 |
| 4,259,211 | 3/1981 | Krabetz et al. | 252/443 |
| 4,341,900 | 7/1982 | Ishii et al. | 562/534 X |
| 4,365,087 | 12/1982 | Kadowaki et al. | 562/534 |
| 4,410,725 | 10/1983 | Decker et al. | 562/534 |
| 4,414,411 | 11/1983 | Decker et al. | 562/534 |
| 4,415,752 | 11/1983 | Decker et al. | 562/534 |
| 4,892,856 | 1/1990 | Kawajiri et al. | 502/247 |
| 5,198,578 | 3/1993 | Etzkorn et al. | 562/534 X |

FOREIGN PATENT DOCUMENTS

| | | |
|---|---|---|
| 2056614 | 6/1972 | Fed. Rep. of Germany . |
| 2251364 | 5/1973 | Fed. Rep. of Germany . |
| 2635031 | 7/1977 | Fed. Rep. of Germany . |
| 2626887 | 12/1977 | Fed. Rep. of Germany . |
| 3002829 | 7/1980 | Fed. Rep. of Germany . |
| 0293859 | 12/1988 | Fed. Rep. of Germany . |

*Primary Examiner*—Arthur C. Prescott
*Attorney, Agent, or Firm*—Oblon, Spivak, McClelland, Maier & Neustadt

[57] ABSTRACT

A process for the catalytic gas-phase oxidation of acrolein to acrylic acid in a fixed-bed reactor with contacting tubes, at elevated temperature on catalytically active oxides with a conversion of acrolein for a single pass of ≧95%, wherein the reaction temperature in the flow direction along the contacting tubes in a first reaction zone before the starting reaction gases containing the reactants enter the contacting tubes is from 260° to 300° C. until an acrolein conversion of from 20 to 40% is reached, and the reaction temperature is subsequently reduced by a total of from 5° to 40° C., abruptly or successively in steps or continuously along the contacting tubes until a methacrolein conversion of ≧95% has been reached, with the proviso that the reaction temperature in this secondary reaction zone is not lower than 240° C.

3 Claims, No Drawings

CATALYTIC GAS-PHASE OXIDATION OF ACROLEIN TO ACRYLIC ACID

The present invention relates to a novel process for the catalytic gas-phase oxidation of acrolein to acrylic acid in a fixed-bed reactor with contacting tubes, at elevated temperature on catalytically active oxides with a conversion of acrolein for a single pass of $\geq 95\%$.

Both acrylic acid itself and esters thereof with lower alcohols are suitable as the starting monomer for the preparation of polymers for a wide variety of applications (for example adhesives).

The preparation of acrylic acid by the catalytic gas-phase oxidation of acrolein is highly exothermic. It is therefore necessary, as a consequence of a number of possible parallel or subsequent reactions, to control the reaction temperature in order to obtain a highly selective conversion of acrolein to acrylic acid.

DE-A 2 635 031 discloses, for acrolein conversions for a single pass of greater than 95%, a way of controlling the variation in the reaction temperature in the catalytic gas-phase oxidation of acrolein to acrylic acid in a fixed-bed reactor with contacting tubes in such a manner that the contacting tubes are surrounded by a salt melt at 270° C.

DE-A 3 002 829 discloses a two-step process for the preparation of acrylic acid by the catalytic gas-phase oxidation of propylene in which the temperature of the acrolein-containing reaction gases from the first oxidation step is adjusted to 250° C. before they enter the second step, and the acrolein-containing reaction gases temperature-controlled in this way are passed, for further oxidation, into a fixed-bed reactor with contacting tubes in which the contacting tubes are surrounded by a salt melt at 280° C. which flows in cocurrent with the reaction gases outside the contacting tubes. DE-A 2 056 614 discloses a two-step process for the preparation of acrylic acid by the catalytic gas-phase oxidation of propylene in which the contact tubes in the second oxidation step are surrounded by a salt melt at from 250° to 272° C., the acrolein-containing reaction gases from the first oxidation step are fed to the second oxidation step in such a manner that they are already at the temperature of the salt bath employed in the second step, and in which the catalyst activity in the second oxidation step increases in the flow direction of the reaction gases.

The known processes have the disadvantage that the variations in reaction temperature which are set implicitly along the contact tubes are not entirely satisfactory with respect to highly selective conversion of acrolein to acrylic acid.

It is an object of the present invention to provide a process for the catalytic gas-phase oxidation of acrolein to acrylic acid in a fixed-bed reactor having contacting tubes, at elevated temperature on catalytically active oxides with a conversion of acrolein for a single pass of $\geq 95\%$, which has a reaction temperature program which is improved with respect to increased selectivity of formation of acrylic acid.

We have found that this object is achieved by a process for the catalytic gas-phase oxidation of acrolein to acrylic acid in a fixed-bed reactor with contacting tubes, at elevated temperature on catalytically active oxides with a conversion of acrolein for a single pass of $\geq 95\%$, wherein the reaction temperature in the flow direction along the contacting tubes (along the reaction axis) in a first reaction zone before the starting reaction gases containing the reactants enter the contacting tubes is from 260° to 300° C. until an acrolein conversion of from 20 to 40% is reached, and the reaction temperature is subsequently reduced by a total of from 5° to 40° C., abruptly or successively in steps or continuously along the contacting tubes until a methacrolein conversion of a $\geq 95\%$ has been reached, with the proviso that the reaction temperature in this secondary reaction zone is not lower than 240° C.

Suitable oxidic catalysts are, inter alia, the materials described in EP-A 293 859, DE-A 2 251 364 and DE-A 2 626 887.

Preference is given to materials of the formula I $$Mo_{12}X_a^1 X_b^2 X_c^3 X_d^4 O_n \qquad (I),$$

where
X$^1$ is vanadium and/or tungsten,
X$^2$ is iron, manganese and/or copper,
X$^3$ is niobium, tantalum, titanium, tin, antimony and/or cerium,
X$^4$ is chromium, cobalt, zirconium, nickel, silicon and/or aluminum,
a is 0.3 to 6,
b is 0 to 6,
c is 0 to 6,
d is 0 to 6 and
n is a number determined by the valency and frequency of the elements other than oxygen in the formula I.

Said oxidic catalysts can be obtained in a conventional manner. They can be prepared, for example, by finely distributing, as starting compounds, suitable salts of the elemental constituents which make up the catalysts, if desired at elevated temperature and with addition of acids or bases, in an aqueous medium by dissolution and/or suspension, mixing the solutions or suspensions, drying the mixture, shaping the resultant material and calcining the product in a stream of air or in an inert atmosphere, for example $N_2$ or $CO_2$, in general at from 250° to 450° C. During shaping, conventional assistants such as lubricants (e.g. graphite) or shaping aids and reinforcing agents, such as glass, asbestos, silicon carbide or potassium titanate microfibers, can be added. In this form, the oxidic materials are expediently prepared for use as unsupported catalysts, the preferred catalyst geometry being hollow cylinders having an external diameter and length of from 4 to 10 mm and a wall thickness of from 1 to 3 mm. However, the catalytically active oxides may also be used in the form of shell catalysts, i.e. on a preshaped carrier material, it being possible for the oxides to be applied to the carrier material, for example, in the form of an aqueous starting solution or suspension, together with subsequent drying and calcination, or as a pre-calcined, powdered material in combination with a binder. Further details are given in DE-A 2 626 887.

It is of course also possible for the catalytically active oxidic materials to be employed in powder form as catalysts.

The oxygen required for the oxidation of the acrolein can be supplied, for example, in the form of air, but also in pure form. Due to the high heat of reaction, the reactants are preferably diluted with an inert gas such as $N_2$, recovered reaction offgases and/or steam. In general, the oxidation is carried out at an acrolein:oxygen:steam:inert gas ratio of from 1:(1 to 3):(0 to 20):(3 to 30), preferably from 1:(1 to 3):(0.5 to 10):(7 to 18). The process is usually carried out using acrolein produced by catalytic gas-phase oxidation of propene. In general, the acrolein-containing reaction gases from this propene oxidation are employed without intermediate purification. The reaction pressure in the process according to the invention is generally from 1 to 3 bar and the total space velocity is preferably from 1000 to 2500 l(s.t.p.)/l/h.

The reaction temperature profile according to the invention can be achieved in a manner known per se, for example by zone heating or cooling of the contacting tubes by means of electrical heating bands or circulating heating fluids, such as melts of salts such as potassium nitrate, sodium nitrite and/or sodium nitrate, or of low-melting metals, such as sodium, tin, mercury and alloys of various metals, or heat-transfer oils; if there is only a single tube, the high heat transfer means that the temperature prevailing inside the tube during the reaction is essentially equal to the external heating or cooling temperature.

However, zone heating or cooling is also possible in multiple-tube fixed-bed reactors, as preferably employed for large-scale industrial implementation of the process according to the invention and described, for example, in DE-A 2 830 765, DE-A 2 201 528, DE-A 1 601 162, DE-A 2 513 405 and U.S. Pat. No. 3,147,084.

Another way of controlling the reaction temperature is to increase or reduce the catalyst activity in zones. This can be done by chemically modifying the active catalyst material or by dilution with deactivated catalyst or inert material. Zone heating/cooling may also be combined with increasing/reducing the catalyst activity in zones. An acrolein conversion of above 99% is preferred. It is particularly advantageous to reduce the reaction temperature by a total of from 15° to 25° C. after the first reaction zone, either abruptly or successively in steps or continuously along the reaction axis until the acrolein conversion has been reached. A stepwise reduction is preferred for technical reasons, generally in from 2 to 4 steps.

Since only finite heat transfer from the heating medium to the reaction gases can be achieved when working on a large industrial scale, in particular if a multiple-tube fixed-bed reactor heated by means of a salt bath is used, it has proven advantageous to feed the starting reaction gases to the first reaction zone after preheating, generally to the reaction temperature. If a temperature of the heating medium of above 260° C., but $\leq 280°$ C., is selected along the first reaction zone, the reaction gases are preferably fed to the first reaction zone after preheating to a temperature from 15° to 20° C. above the temperature of the heating medium at the beginning of the first reaction zone. If the temperature of the heating medium along the first reaction zone is in the range from 280° to not more than 300° C., the reaction gases are preferably fed to the first reaction zone after preheating to a temperature only up to 10° C. above the temperature of the heating medium at the beginning of the first reaction zone. If the temperature of the heating medium along the first reaction zone is constant, a continuously falling reaction temperature is established in the flow direction along the first reaction zone. This has proven particularly advantageous, in particular if the continuous drop in reaction temperature is continued in the flow direction along the second reaction zone. It is of course possible for the continuous drop in reaction temperature along the reaction axis to be approximated by successive stepwise drops in temperature. The drop in reaction temperature along the first reaction zone in the flow direction is preferably from 5° to 20° C.

Typical contacting tubes comprise corrosion- and heat-resistant steel (e.g. V2A), and have a wall thickness of about 2 mm and an internal diameter of 25 mm. The number of these tubes in a multiple-tube fixed-bed reactor is generally from 10000 to 40000. The conversion U and selectivity S are defined as follows in this document:

$$U = \frac{\text{number of mols of acrolein reacted}}{\text{number of mols of acrolein employed}} \times 100$$

$$S = \frac{\text{number of mols of acrylic acid formed}}{\text{number of mols of acrolein reacted}} \times 100$$

EXAMPLES B1 TO B4 AND COMPARATIVE EXAMPLES V1 TO V2

A steel tube (V2A, wall thickness 2 mm, internal diameter 25 mm) zone-heated by means of electrical heating bands was filled to a level of 3 m with a catalyst as described in Example 1 of DE-A 2 626 887 and charged with 2400 l(s.t.p.)/l/h of a gas mixture having the composition 4.5% by volume of acrolein,
6.5% by volume of oxygen,
10.0% by volume of steam and
79.0% by volume of nitrogen, which was preheated to various temperatures $T^1$ depending on the example. The temperature of the electrical heating bands was subsequently adjusted to $T^2$ along the first reaction zone to an acrolein conversion of 40% and then to $T^3$ until the reaction gases leave the tube. The end conversion $U_{end}$ was determined by the length of the second reaction zone. The results obtained (selectivity $S_{end}$ of the acrylic acid formation) are shown in the table.

TABLE

|    | $T^1$ | $T^2$ | $T^3$ | $U_{end}$ | $S_{end}$ |
|----|-------|-------|-------|-----------|-----------|
| B1 | 280   | 280   | 266   | 99.2      | 96.8      |
| B2 | 285   | 285   | 264   | 99.4      | 97.5      |
| B3 | 290   | 290   | 258   | 99.1      | 96.1      |
| B4 | 290   | 285   | 263   | 99.1      | 97.3      |
| V1 | 270   | 270   | 270   | 99.2      | 95.4      |
| V2 | 250   | 250   | 298   | 99.3      | 94.8      |

We claim:

1. A process for the catalytic gas-phase oxidation of acrolein to acrylic acid in a fixed-bed reactor with contacting tubes, at elevated temperature on catalytically active oxides with a conversion of acrolein for a single pass of $\geq 95\%$, wherein the reaction temperature in the flow direction along the contacting tubes in a first reaction zone before the starting reaction gases containing the reactants enter the contacting tubes is from 260° to 300° C. until an acrolein conversion of from 20 to 40% is reached, and the reaction temperature is subsequently reduced by a total of from 5° to 40° C., abruptly or successively in steps or continuously along the contacting tubes until an acrolein conversion of $\geq 95\%$ has been reached, with the proviso that the reaction temperature in this secondary reaction zone is not lower than 240° C.

2. A process as claimed in claim 1, wherein the reaction temperature of the reaction gases drops successively in the flow direction along the contacting tubes until they leave the contacting tubes.

3. A process as claimed in claim 1, wherein the oxidic catalysts are materials of the formula I $$Mo_{12}X^1_a X^2_b X^3_c X^4_d O_n \qquad (I),$$

where
- $X^1$ is vanadium and/or tungsten,
- $X^2$ is iron, manganese and/or copper,
- $X^3$ is niobium, tantalum, titanium, tin, antimony and/or cerium,
- $X^4$ is chromium, cobalt, zirconium, nickel, silicon and/or aluminum,
- a is 0.3 to 6,
- b is 0 to 6,
- c is 0 to 6,
- d is 0 to 6 and
- n is a number determined by the valency and frequency of the elements other than oxygen in the formula I.

* * * * *